United States Patent [19]

Sawa et al.

[11] Patent Number: 5,187,094
[45] Date of Patent: Feb. 16, 1993

[54] METHOD FOR THE PREPARATION OF OPTICALLY ACTIVE 3-HYDROXYPYRROLIDINE DERIVATIVES

[75] Inventors: Ikuo Sawa; Natsuki Mori; Shunichi Maemoto, all of Takasago; Hidetoshi Kutsuki, Kobe; Junzo Hasegawa, Akashi, all of Japan

[73] Assignee: Kanegafuchi Kagaku Kogyo Kabushiki Kaisha, Osaka, Japan

[21] Appl. No.: 764,119

[22] Filed: Sep. 24, 1991

Related U.S. Application Data

[63] Continuation of Ser. No. 407,394, Sep. 6, 1989, abandoned.

[51] Int. Cl.$^5$ .............................................. C12P 41/00
[52] U.S. Cl. .................................. 435/280; 435/121; 435/135
[58] Field of Search ......................... 435/121, 280, 135

[56] References Cited

U.S. PATENT DOCUMENTS 4,916,074  4/1990  Yoshida et al. ..................... 435/280

FOREIGN PATENT DOCUMENTS

| 247620 | 12/1987 | European Pat. Off. ............ 435/135 |
| 118428 | 9/1980 | Japan .................................. 435/135 |
| 60-23328 | 2/1985 | Japan . |
| 78596 | 5/1985 | Japan .................................. 435/280 |
| 61-63652 | 4/1986 | Japan . |
| 219387 | 9/1988 | Japan .................................. 435/135 |
| 1-141600 | 6/1990 | Japan . |

OTHER PUBLICATIONS

"Chiral Synthesis via Organoboranes. 6. Hydroboration. 74. Asymmetric Hydroboration of Representative Heterocyclic Olefins with Diisopinocampheylborane. Synthesis of Heterocyclic Boronates and Heterocyclic Alcohols of Very High Enantiomeric Purity", Brown et al., J. Am. Chem. Soc. 1986, vol. 108, No. 8, pp. 2049–2054.

"Synthesis of 3S-Pyrrolidinol from L-Glutamic Acid", Harris et al., Synthetic Communications, vol. 16, No. 14, (1986), pp. 1815–1822.

*Primary Examiner*—Carolyn Elmore
*Assistant Examiner*—Shailendra Kumar
*Attorney, Agent, or Firm*—Armstrong, Westerman, Hattori, McLeland & Naughton

[57] ABSTRACT

A method for the preparation of optically active 3-hydroxypyrrolidine derivatives is disclosed, which comprises the steps of: hydrolyzing a mixture of (R)- and (S)-N-benzyl-3-acyloxypyrrolidine by the use of microorganisms or enzymes with stereospecific esterase activity; and separating optically active N-benzyl-3-hydroxypyrrolidine and optically active N-benzyl-3-acyloxypyrrolidine from the hydrolysate obtained in the foregoing step.

8 Claims, No Drawings

METHOD FOR THE PREPARATION OF OPTICALLY ACTIVE 3-HYDROXYPYRROLIDINE DERIVATIVES

This application is a continuation of application Ser. No. 407,394, filed Sep. 6, 1989, now abandoned.

BACKGROUND OF THE INVENTION

1. Field of the Invention

This invention relates to a method for the preparation of optically active 3-hydroxypyrrolidine derivatives (i.e., both enantiomers of optically active N-benzyl-3-hydroxypyrrolidine and also of optically active N-benzyl-3-acyloxypyrrolidine), which are useful as intermediates for the syntheses of pharmaceutical products, agricultural chemicals, and the like.

2. Description of the Prior Art

As a method for the preparation of (S)-N-benzyl-3-hydroxypyrrolidine, a synthetic process that uses L-malic acid as a raw material is known (Japanese Laid-Open Patent Publication No. 61-63652). However, in that process, a portion of the product is racemized, and therefore, optical resolution with use of D-mandelic acid must be done to improve the optical purity of the product. Another method is known that comprises the step of reducing N-benzyl-3-pyrroline with (+)-Diisopinocampheylborane, used as an asymmetric reducing agent [J. Am. Chem. Soc., 108, 2049 (1986)]. Moreover, there is a method for the derivation of (S)-3-hydroxypyrrolidine without a benzyl group at the N-position from L-glutamic acid [Synthetic Communication, 16, 1815 (1986)]. A method for obtaining (R)-3-hydroxypyrrolidine by the decarboxylation of trans-4-hydroxy-L-proline is known (Japanese Laid-Open Patent Publication No. 60-23328). Therefore, optically active N-benzyl-3-hydroxypyrrolidine can also be obtained by benzylation of these 3-hydroxypyrrolidine products. However, all of these methods require many steps and special reagents, and therefore do not permit the production of N-benzyl-3-hydroxypyrrolidine on an industrial scale.

SUMMARY OF THE INVENTION

The method for the preparation of optically active 3-hydroxypyrrolidine derivatives of this invention, which overcomes the above-discussed and numerous other disadvantages and deficiencies of the prior art, comprises the steps of: hydrolyzing a mixture of (R)- and (S)-N-benzyl-3-acyloxypyrrolidine of the formula:

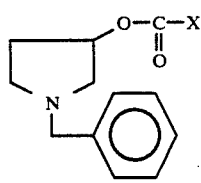
[I]

wherein X is hydrogen or a substituted or unsubstituted alkyl or alkenyl group containing 1 to 17 carbon atoms, by the use of microorganisms or enzymes with stereospecific esterase activity; and separating from the hydrolysate obtained in the foregoing step the optically active N-benzyl-3-hydroxypyrrolidine of the formula:

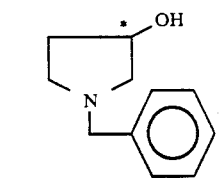
[II]

and the optically active N-benzyl-3-acyloxypyrrolidine of the formula:

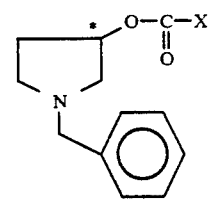
[I']

wherein X is as defined above.

In a preferred embodiment, the compound of the formula [II] is optically active (R)-N-benzyl-3-hydroxypyrrolidine of the formula:

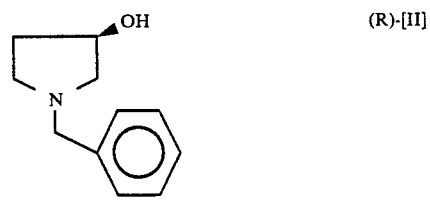
(R)-[II]

and the compound of the formula [I'] is optically active (S)-N-benzyl-3-acyloxypyrrolidine of the formula:

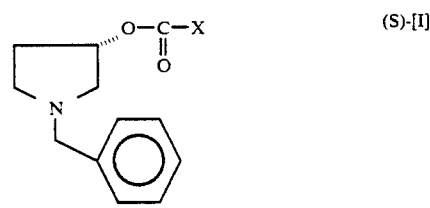
(S)-[I]

wherein X is as defined above.

In a preferred embodiment, the microorganisms or enzymes with stereospecific esterase activity are of the genus Pseudomonas, Mucor, or Alcaligenes, or enzymes derived from these microorganisms.

In a preferred embodiment, the compound of the formula [II] i optically active (S)-N-benzyl-3-hydroxypyrrolidine of the formula:

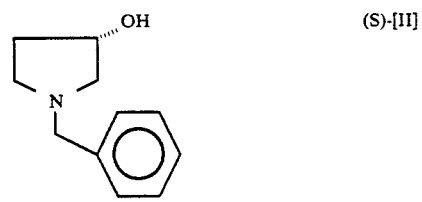
(S)-[II]

and the compound of the formula [I'] is optically active (R)-N-benzyl-3-acyloxypyrrolidine of the formula:

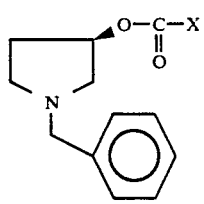

wherein X is as defined above.

In a preferred embodiment, the microorganisms or enzymes with stereospecific esterase activity are of the genus Rhizopus or Phycomyces, or are enzymes derived from these microorganisms.

In a preferred embodiment, the enzyme is lipase.

In a preferred embodiment, the microorganisms or enzymes with stereospecific esterase activity are immobilized on a water-insoluble carrier or support.

In a preferred embodiment, the optically active N-benzyl-3-hydroxypyrrolidine and the optically active N-benzyl-3-acyloxypyrrolidine are separated from each other by column chromatography with an inorganic or synthetic adsorbent used as a support.

In a preferred embodiment, the optically active N-benzyl-3-acyloxypyrrolidine is separated from the optically active N-benzyl-3-hydroxypyrrolidine by extraction with a hydrophobic solvent.

The present inventors have previously discovered that the racemate (RS)-N-benzyl-3-acyloxypyrrolidine [I], which is a mixture of the (R)- and (S)-forms in equal amounts, can readily be synthesized by the reaction of fatty acid halides and (RS)-N-benzyl-3-hydroxypyrrolidine, which is a novel racemate that can readily be synthesized from inexpensive substances such as DL-malic acid, and the present inventors have already filed a patent application concerning this discovery. Subsequently, the present inventors investigated the optical resolution of this novel racemic mixture of (R)- and (S)-N-benzyl-3-acyloxypyrrolidine [I] by asymmetric hydrolysis using microorganisms or enzymes. As a result, the present inventors discovered the existence of microorganisms and enzymes capable of causing stereospecific hydrolysis of the compound [I], thereby producing the corresponding optically active compound [II]. After conduction of the hydrolytic reaction using such microorganisms or enzymes, optically active N-benzyl-3-hydroxypyrrolidine [II] and the enantiomeric form of optically active N-benzyl-3-acyloxypyrrolidine [I] can be obtained by simple separation procedures. Furthermore, by treatment of this optically active N-benzyl-3-acyloxypyrrolidine to either basic hydrolysis or else to hydrolysis using microorganisms or enzymes with stereospecific esterase activity that have been discovered in this invention or using enzymes without stereospecific activity (e.g., lipases), optically active N-benzyl-3-hydroxypyrrolidine that retains the original configuration can be obtained. Thus, by use of microorganisms or enzymes with either stereospecific activity, both the enantiometric (R)- and (S)-forms of N-benzyl-3-hydroxypyrrolidine can be obtained.

Thus, the invention described herein makes possible the objective of providing a more economical method for the preparation of both enantiomers of optically active N-benzyl-3-hydroxypyrrolidine and also of optically active N-benzyl-3-acyloxypyrrolidine using microorganisms or enzymes with stereospecific esterase activity to bring about stereospecific hydrolysis of a mixture of (R)- and (S)-N-benzyl-3-acyloxypyrrolidine.

DESCRIPTION OF THE PREFERRED EMBODIMENTS

The (R)- and (S)-N-benzyl-3-acyloxypyrrolidine of the formula:

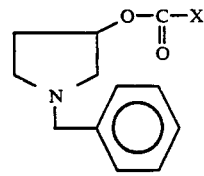

that is used as a substrate in this invention can be either a racemic mixture of the (R)- and (S)-forms in equal amounts, or a mixture of the (R)- and (S)-form in unequal amounts. The substituent X in the formula [I] can be hydrogen, or a straight-chain or branched alkyl or alkenyl group containing 1 to 17 carbon atoms. These substituents themselves may be unsubstituted or may be substituted by halogens, etc. Specific examples of the substituent include straight-chain or branched unsubstituted alkyl or alkenyl groups such as methyl, ethyl, ethylene, n-propyl, isopropyl, 1-propylene, n-butyl, isobutyl, 1-butylene, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, and n-octadecyl groups; and halogen-substituted alkyl groups such as chloromethyl, dichloromethyl, trifluoromethyl, 2-chloroethyl, 3-chloropropyl, and 4-chlorobutyl groups.

The microorganisms or enzymes with stereospecific esterase activity, capable of causing stereospecific hydrolysis of the compound [I] to produce the optically active compound [II] can readily be found by the screening procedures described below. For example, 10 ml of nutrient medium suitable for the growth of microorganisms is placed in a large test tube, and after inoculation of the microorganism to be tested, the culture is incubated with shaking at 25°–35° C. for 1–3 days. Thereafter, 2% (W/V) of (RS)-N-benzyl-3-butyryloxypyrrolidine is added to this culture, and the mixture is allowed to react at 20°–35° C. for 1–3 days while the mixture is adjusted to pH 5–7 by the addition of NaOH. The reaction mixture is then adjusted to pH 2.0 by the addition of $H_2SO_4$, and the butyric acid produced is extracted with two volumes of ethyl acetate and assayed by gas chromatogtaphy at 140° C. with a column ($\phi$ 0.3×100 cm; packed with Shimadzu FAL-M 6%/Shimalite) to measure the degree of progress of the hydrolysis. First, those strains of microorganisms are chosen such that the reaction will be extremely slow when approximately 0.5 equivalent of butyric acid has been produced with respect to the substrate added.

Next, the scale of the reaction is increased 50-fold, and the culture and hydrolysis procedures described above are performed again. After completion of the reaction, the reaction mixture is extracted four times with 500-ml portions of dichloromethane, and the solvent is removed from the extract under reduced pressure. The extract is then put on a silica gel column (packed with 250 g of Wakogel C-200) and the unreacted N-benzyl-3-butyryloxypyrrolidine is eluted with a 10:2 hexane-ethyl acetate mixture. Then, the N-benzyl- 3-hydroxypyrrolidine produced in the above reaction is eluted with ethyl acetate. These fractions are concentrated to yield optically active N-benzyl-3-butyryloxypyrrolidine and optically active N-benzyl-3-hydroxypyrrolidine in oily form. When the optically active N-benzyl-3-butyryloxypyrrolidine obtained in this manner is hydrolyzed with a sodium hydroxide solution, optically active N-benzyl-3-hydroxypyrrolidine is obtained. These products are purified by distillation, and by measurement of their specific rotation, it can readily be found whether the microorganisms tested have stereospecific esterase activity. In the screening of enzymes derived from various sources, a solution containing 0.5 g of the enzyme dissolved in 10 ml of 0.1 M phosphate buffer solution is used in place of the above-mentioned microorganism culture, and the same analytical procedure as described above can be used. Moreover, microorganisms or enzymes capable of such stereo-specific hydrolysis of N-benzyl-3-butyryloxypyrrolidine can also have stereospecific hydrolytic activity with respect to the various types of N-benzyl-3-acyloxypyrrolidine mentioned above.

As microorganisms with stereospecific esterase activity capable of causing stereospecific hydrolysis of a mixture of (R)- and (S)-N-benzyl-3-acyloxypyrrolidine to produce the compounds (R)-[II] and (S)-[I], there can be mentioned, for example, various microorganisms belonging to the genus *Pseudomonas, Mucor,* or *Alcaligenes*, and more particularly, the strains *Pseudomonas fluorescens* (IFO 3081), *Pseudomonas aeruginosa* (IFO 3080), *Mucor javanicus* (IFO 4569), and *Alcaligenes eutrophus* (ATCC 17697).

These microorganisms can be used in the form of cultures, but enzymes extracted and purified from these cultures or from the cells of the microorganisms can also be used. Moreover, various commercially available enzymes can be used directly. For example, commercially available enzymes suitable for the purpose of this invention include lipoprotein lipase LPL Amano 3 (derived from a Pseudomonas strain, and available from Amano Seiyaku, Inc.), lipase M-AP10 (derived from a Mucor strain and available from Amano Seiyaku, Inc.), and lipase PL (derived from a Alcaligenes strain and available from Meito Sangyo, Inc.).

On the other hand, as microorganisms with stereospecific esterase activity capable of causing stereospecific hydrolysis of a mixture of (R)- and (S)-N-benzyl-3-acyloxypyrrolidine to produce the compounds (S)-[II] and (R)-[I], there can be mentioned, for example, various microorganisms belonging to the genus *Rhizopus* or *Phycomyces*, and more particularly the strains *Rhizopus japonicus* (IFO 4758), *Rhizopus delemer* (IFO 4697), and *Phycomyces nitens* (IFO 5694).

These microorganisms can be used in the form of cultures, but enzymes extracted and purified from these cultures or the cells of the microorganisms can also be used. Moreover, various commercially available enzymes can be used directly. For example, commercially available enzymes suitable for the purpose of this invention include lipase PN (derived from a Phycomyces strain and available from Wako Pure Chemical Industries, Ltd. ), lipase (derived from a Rhizopus strain and available from Seikagaku Kogyo, Inc.), lipase "Saiken" 100 (derived from a Rhizopus strain and available from Osaka Bacteriological Laboratories, Inc.), and neurase (derived from a Rhizopus strain and available from Amano Seiyaku, Inc.).

The hydrolysis can be conducted by addition of the substrate [I] to the concentration of 0.5-75% (W/V) to a culture containing the microorganisms or to an enzymatic extract or an aqueous solution of the enzyme, and subsequent incubation of the mixture at 10°-55° C. with agitation. The appropriate ratio of the enzyme to the substrate [I] depends on the level of activity of the enzyme, and usually ranges from 1:1 to 1:1000. The hydrolysis is conducted at pH 5.0-8.5. If the pH varies during the course of the reaction, the optimal pH should be maintained by the addition of a suitable acid or alkaline solution.

The microorganisms or enzymes can be immobilized on a water-insoluble carrier or support and used repeatedly. The microorganisms can be immobilized by use of carriers such as acrylamide polymers, urethane polymers, polymers derived from ethylene glycol derivatives, carrageenan, and calcium alginate. The enzymes can be immobilized by use as supports, for example, of synthetic adsorbents such as Amberlite XAD- 7, Amberlite XAD-2, Daiaion HP20, Daiaion HP2MG, and Octyl-Sepharose CL-4B. The solubility of the substrate [I] in water is generally low, but this does not preclude a satisfactory rate of reaction if agitation is sufficient. However, to facilitate the rapid progress of the reaction, hydrophilic solvents such as acetone and ethanol, or surfactants, may be added to an extent that does not adversely affect the reaction.

The reaction is monitored by gas chromatographic analysis of the organic acids generated in the hydrolysis. The reaction may be stopped at the point when 0.5 equivalent of the organic acid with respect to substrate [II] added have been generated.

The acid component [II] and the residual substrate [I] can be separated from each other in the following way. Because of a hydrophobic organic solvent (e.g., hexane, cyclohexane, petroleum ether, methylene chloride, chloroform, or carbon tetrachloride), the substrate [I] alone, or the substrate [I] containing a certain amount of the acid component [II] is extracted from the reaction mixture adjusted to pH 4.0-8.5, and a pure form of each product can be obtained by silica gel chromatography (with a hexane-acetone eluant), if necessary. The acid component [II] present in the reaction mixture can be completely recovered by extraction with the above-mentioned solvent after adjustment of the reaction mixture to pH 9-14 by the addition of NaOH or the like. Because the compound [I] undergoes hydrolysis under alkaline conditions, extraction of the compounds [II] and [I] under alkaline conditions may cause a decrease in the optical purity of compound [II], which is undesirable.

The compounds [I] and [II] can be separated by the above-mentioned silica gel chromatography, or alternatively by use of other inorganic adsorbents (e.g., Florisil, alumina, or zeolite) or synthetic adsorbents (e.g., Amberlite XAD-7, Amberlite XAD-2, Daiaion HP21, Daiaion HP2MG, or Octyl-Sepharose CL-4B). The compounds [I] and [II] with a long carbon chain can also be separated by distillation.

The optically active compound [I] can be used as a starting material for synthesis in unmodified form, and can readily be converted into the compound [II] while the optical activity is retained, by either chemical hydrolysis using alkali such as NaOH, KOH, or Ca(OH)$_2$, or by hydrolysis using an esterase or microorganism with different stereospecific activity.

The optical purity of compounds [II] and [I] can be measured as follows. The compound [I] is hydrolyzed and converted into the compound [II] by the procedure described above. The compound [II] is allowed to react, in methylene chloride, with an equimolar amount of p-toluenesulfonyl chloride, and the products so obtained are treated by high performance liquid chromatography (HPLC; column, Chiralcell OB (Nihon Bunko), φ 0.46×25 cm; eluant, hexaneisopropanol (20:1); flow rate, 1.5 ml/min.; detection wavelength 221 nm; retention times, 36.7 min. for the (R)-form and 51.3 min. for the (S)-form) to measure the optical purity.

EXAMPLE 1

First, 0.1 g of lipoprotein lipase (LPL Amano 3, derived from a Pseudomonas strain and available from Amano Seiyaku, Inc.) and 10 g of the racemate (RS)-N-benzyl-3-butyryloxypyrrolidine were added to 100 ml of 0.1 M phosphate buffer solution (pH 7.0). After adjustment of the mixture to pH 7.0 by the addition of HCl, this mixture was allowed to react at 40° C. with agitation for 28 hours. The reaction mixture was extracted three times with 100-ml portions of hexane, and the solvent was removed from the extract under reduced pressure to yield 4.95 g of (S)-N-benzyl-3-butyryloxypyrrolidine in oily form. The residue remaining after the above hexane extraction was adjusted to pH 13 by the addition of NaOH, and then extracted three times with 100-ml portions of hexane. The solvent was removed from the extract under reduced pressure to yield 3.42 g of (R)-N-benzyl-3-hydroxypyrrolidine in oil form. The (S)-N-benzyl-3-butyryloxypyrrolidine obtained as described above was treated by vacuum distillation at 132°–137° C./3 mm Hg to yield 4.5 g of a colorless, transparent, purified product. The specific rotation of this product was $[a]_D^{20} -19.2°$ (c=5, MeOH). The NMR and IR spectra of this product coincided with those of the reference sample, and the results obtained by elemental analysis agreed with the calculated values.

Next, 50 ml of 1 N-NaOH was added to the (S)-N-benzyl-3-butyryloxypyrrolidine obtained above, and hydrolysis was performed while the mixture was heated. The reaction mixture was then extracted three times with 50 ml portions of methylene chloride, and the solvent was removed under reduced pressure to yield 3.31 g of (S)-N-benzyl-3-hydroxypyrrolidine. This crude product was vacuum-distilled at 111° C./2 mm Hg to yield 3.00 g of a colorless oily product. The NMR and IR spectra of this product coincided with those of the reference sample, and the results obtained by elemental analysis agreed well with the calculated values. The specific rotation of this product was $[a]_D^{20} -3.79$ (c=5, MeOH), and the measurement by HPLC showed that the optical purity was 100% e.e. The specific rotation of the distilled (R)-N-benzyl-3-hydroxypyrrolidine was $[a]_D^{20} +3.73°$ (c=5, MeOH), and the optical purity was 99% e.e.

EXAMPLE 2–14

First, 45.5 mmol of the racemate (RS)-N-benzyl-3-acyloxypyrrolidine, the various acyl substituents of which are listed in Table 1, was added to 100 ml of 0.1 M phosphate buffer (pH 7.0), and then 0.1–1.0 g of lipoprotein lipase (LPL Amano 3) was added thereto. After adjustment of the mixture to pH 7.0 by the addition of HCl, the mixture was then allowed to react at 40° C. with agitation for 24–72 hours. The reaction was stopped when 50% of the substrate had been hydrolyzed. Five repeated extractions from the reaction mixture with 100 ml portions of methylene chloride yielded a mixture of unreacted (S)-N-benzyl-3-acyloxypyrrolidine and the hydrolyzed product (R)-N-benzyl-3-hydroxypyrrolidine. After removal of the solvent under reduced pressure, the residue was put on a silica gel column (packed with 200 g of Wako-C200) and eluted with a hexane-ethyl acetate mixture (10:2 to 5:10) to separate the (S)-N-benzyl-3-acyloxypyrrolidine and the (R)-N-benzyl-3-hydroxypyrrolidine. The (S)-N-benzyl-3-acyloxypyrrolidine obtained was hydrolyzed in the same way as described in Example 1, and then the optical purities were measured. The results are shown in Table 1.

TABLE 1

| | Substrate | | | Products | | | |
|---|---|---|---|---|---|---|---|
| | | | | (S)-N-benzyl-3-acyloxypyrrolidine | | (R)-N-benzyl-3-hydroxypyrrolidine | |
| Example No. | (RS)-N-benzyl-3-acyloxypyrrolidine Substituent: X | Amount of enzyme added (g) | Reaction time (hr) | Yield (g) | Optical purity[1] (%) | Yield (g) | Optical purity (%) |
| 2 | Methyl | 0.1 | 48 | 4.6 | 100 | 3.7 | 98 |
| 3 | Ethyl | 0.1 | 24 | 4.9 | 100 | 3.6 | 98 |
| 4 | n-Propyl | 0.1 | 28 | 5.2 | 100 | 3.5 | 99 |
| 5 | n-Butyl | 1.0 | 24 | 5.3 | 100 | 3.5 | 99 |
| 6 | n-Pentyl | 0.1 | 40 | 5.5 | 100 | 3.4 | 98 |
| 7 | n-Hexyl | 0.1 | 24 | 5.9 | 100 | 3.6 | 98 |
| 8 | n-Heptyl | 0.1 | 24 | 6.4 | 100 | 3.3 | 97 |
| 9 | n-Nonyl | 0.1 | 24 | 7.0 | 100 | 3.5 | 98 |
| 10 | n-Tridecyl | 1.0 | 20 | 8.2 | 93 | 3.4 | 86 |
| 11 | n-Pentadecyl | 1.0 | 48 | 8.7 | 87 | 3.7 | 61 |
| 12 | n-Heptadecyl | 1.0 | 72 | 9.3 | 77 | 3.6 | 52 |
| 13 | Isopropyl | 2.0 | 24 | 5.1 | 99 | 3.4 | 95 |

TABLE 1-continued

| | Substrate | | | Products | | | |
|---|---|---|---|---|---|---|---|
| | (RS)-N-benzyl-3-acyloxypyrrolidine | | | (S)-N-benzyl-3-acyloxypyrrolidine | | (R)-N-benzyl-3-hydroxypyrrolidine | |
| Example No. | Substituent: X | Amount of enzyme added (g) | Reaction time (hr) | Yield (g) | Optical purity[1] (%) | Yield (g) | Optical purity (%) |
| 14 | 3-Chloropropyl | 0.1 | 32 | 5.7 | 86 | 3.7 | 93 |

[1] The (S)-N-benzyl-3-acyloxypyrrolidine was hydrolyzed under alkaline conditions into the corresponding (S)-N-benzyl-3-hydroxypyrrolidine. After tosylation of the (S)-N-benzyl-3 hydroxypyrrolidine, the optical purity of the product was measured by HPLC.

EXAMPLE 15

First, 2 g of lipoprotein lipase (LPL Amano 3) was suspended in 40 ml of 0.05 M phosphate buffer (pH 7.0), and 40 g of Amberlite XAD-7 was added thereto. This mixture was agitated overnight, during which time the enzyme was adsorbed onto the resin. The resin was filtered and washed with about 500 ml of 0.05 M phosphate buffer (pH 7.0) to remove the unadsorbed enzyme. The resin with the enzyme adsorbed was packed into a column ($\phi$ 2.2×15 cm), which was kept at 33° C. during the addition of 5 g of (RS)-N-benzyl-3-hexanoyloxypyrrolidine, and then (R)-N-benzyl-3-hydroxypyrrolidine was eluted by passage of 500 ml of 0.05 M phosphate buffer (pH 7.0) through the column. Next, 500 ml of hexane was passed through the column to elute the unreacted (S)-N-benzyl-3-hexanoyloxypyrrolidine.

The eluate containing (R)-N-benzyl-3-hydroxypyrrolidine was concentrated to 50 ml under reduced pressure, and then adjusted to pH 13 by the addition of NaOH. The concentrate was extracted three times with 100-ml portions of methylene chloride. After removal of the solvent under reduced pressure, the extract was vacuum-distilled to yield 1.32 g of (R)-N-benzyl-3-hydroxypyrrolidine in colorless oily form. The specific rotation of this product was $[\alpha]_D^{20}$ +3.75° (c=5, MeOH), and the measurement by HPLC showed that the optical purity was 99% e.e.

After removal of hexane from the eluate containing (S)-N-benzyl-3-hydroxypyrrolidine under reduced pressure, vacuum distillation of the residue (bp. 160° C./3 mm Hg) yielded 2.21 g of (S)-N-benzyl-3-hexanoyloxypyrrolidine in colorless oily form. The specific rotation of this product was $[\alpha]_D^{20}$ −15.3° (c=5, MeOH). This (S)-N-benzyl-3-hexanoyloxypyrrolidine was further hydrolyzed under alkaline conditions to produce the corresponding (S)-N-benzyl-3-hydroxypyrrolidine. After tosylation, the optical purity of this product was found by HPLC to be 100% e.e.

EXAMPLES 16-22

First, 1500 ml of a nutrient liquid medium (pH 7.0) containing 2% glucose, 0.5% yeast extract, 0.3% meat extract, 0.3% peptones, and 1% olive oil was placed in a 3 l minijar, and sterilized by being heated at 120° C. for 20 min. One of the strains of microorganisms listed in Table 2 was inoculated into this jar, which was incubated at 30° C. for 40 hours with ventilation at 1 vvm and stirring at 500 rpm. The culture liquid was then adjusted to pH 7.0, and 5 g of (RS)-N-benzyl-3-hexanoyloxypyrrolidine was added thereto. This mixture was allowed to react at 30° C. for 48 hours. After the reaction, the cells of the microorganisms were removed by centrifugation and the supernatant was extracted three times with equal volumes of hexane to recover the unreacted N-benzyl-3-hexanoyloxypyrrolidine.

Next, the residue remaining after the above hexane extraction was adjusted to pH 13 by the addition of NaOH, and the mixture was then extracted three times with equal volumes of hexane to yield the hydrolyzed N-benzyl-3-hydroxypyrrolidine. After removal of the solvent under reduced pressure, distillation yielded colorless, transparent N-benzyl-3-hydroxypyrrolidine. After tosylation, the optical purity of this product was measured by HPLC. The results with the different strains of microorganisms are shown in Table 2.

TABLE 2

| | | N-benzyl-3-hydroxypyrrolidine produced | | |
|---|---|---|---|---|
| Example No. | Strain | Yield (g) | Configuration | Optical purity (%) |
| 16 | Pseudomonas fluorescens (IFO 3081) | 0.9 | R | 97 |
| 17 | Pseudomonas aeruginosa (IFO 3080) | 1.0 | R | 96 |
| 18 | Mucor javanicus (IFO 4569) | 1.2 | R | 70 |
| 19 | Alcaligenes eutrophus (ATCC 17697) | 1.1 | R | 42 |
| 20 | Rhizopus juponicus (IFO 4758) | 1.0 | S | 83 |
| 21 | Rhizopus delemer (IFO 4697) | 0.8 | S | 72 |
| 22 | Phycomyces nitens (IFO 5694) | 0.7 | S | 68 |

EXAMPLES 23-28

First, 10 g of (RS)-N-benzyl-3-hexanoyloxypyrrolidine and one of the commercially available enzymes listed in Table 3 were added to 100 ml of 0.1 M phosphate buffer (pH 7.0). This mixture was allowed to react at 40° C. with agitation for 22-120 hours. Then, the unreacted (RS)-N-benzyl-3-hexanoyloxypyrrolidine was recovered by three extractions from the reaction mixture with equal volumes of hexane. The aqueous phase was then adjusted to pH 13 by the addition of NaOH, and the hydrolyzed N-benzyl-3-hydroxypyrrolidine was obtained by three extractions with equal volumes of hexane. After removal of the solvent under reduced pressure, distillation yielded purified N-benzyl-3-hydroxypyrrolidine in colorless, transparent, oily form. After tosylation, the optical purity of this purified product was measured by HPLC. The results with the different enzymes used are shown in Table 3.

TABLE 3

| Example No. | Enzyme (source) | | N-benzyl-3-hydroxy-pyrrolidine produced | | |
|---|---|---|---|---|---|
| | Amount of enzyme added (g) | Reaction time (hr) | Yield (g) | Configuration | Optical purity |
| 23 | Lipase M-AP10 (derived from a Mucor strain and available from Amano Seiyaku, Inc.) 10 | 120 | 1.2 | R | 59 |
| 24 | Lipase PL (derived from a Alcaligenes strain and available from Meito Sangyo, Inc.) 2 | 22 | 3.0 | R | 20 |
| 25 | Lipase PN (derived from a Phycomyces strain and available from Wako Pure Chemical Industries, Ltd.) 10 | 120 | 0.8 | S | 49 |
| 26 | Lipase (derived from a Rhizopus strain and available from Seikagaku Kogyo, Inc.) 10 | 120 | 0.7 | S | 43 |
| 27 | Lipase "Saiken" 100 (derived from a Rhizopus strain and available from Osaka Bacteriological Laboratories, Inc.) 10 | 120 | 1.1 | S | 61 |
| 28 | Neurase (derived from a Rhizopus strain and available from Amano Seiyaku, Inc.) 2 | 27 | 1.0 | S | 92 |

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A method for the preparation of optically active (R)-N-benzyl-3-hydroxypyrrolidine of the formula (R)-[II]:

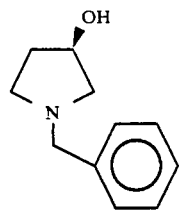
(R)-[II]

comprising the steps of:
(1) hydrolyzing a mixture of (R)- and (S)-N-benzyl-3-acyloxypyrrolidine of the formula [I]:

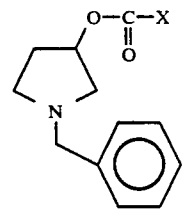
[I]

wherein X is hydrogen or a substituted or unsubstituted alkyl or alkenyl group containing 1 to 17 carbon atoms, by the use of microorganisms selected from the group consisting of Pseudomonas fluorescens IFO 3081, Pseudomonas aeruginasa IFO 3080, and Mucor javanicus IFO 4569, or the enzyme LPL Amano 3, said microorganisms and enzyme having a stereospecific esterase activity for (R)-N-benzyl-3-acyloxypyrrolidine of the formula (R)-[I]:

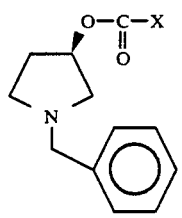
(R)-[I]

wherein x is as defined as above; and
(2) separating form the hydrolysate in the foregoing step (1), (R)-N-benzyl-3-hydroxypyrrolidine of the formula (R)-[II] and (S)-N-benzyl-3-acyloxypyrrolidine of the formula (S)-[I]:

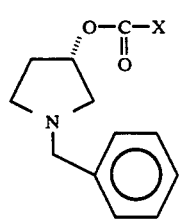
(S)-[I]

wherein X is as defined above.

2. A method for the preparation of optically active (S)-N-benzyl-3-hydroxypyrrolidine of the formula (S)-[II]:

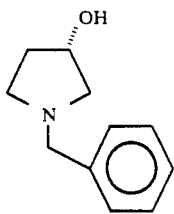
(S)-[II]

comprising the steps of:
(1) hydrolyzing a mixture of (R)- and (S)-N-benzyl-3-acyloxypyrrolidine of the formula [I]:

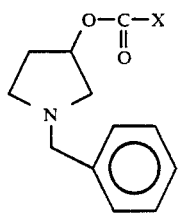
[I]

wherein x is hydrogen or a substituted or unsubstituted alkyl or alkenyl group containing 1 to 17 carbon atoms, by the use of Rhizopus japonicus IFO 4758 or Rhizopus delemer IFO 4697, or the enzyme Neurase, said microorganisms and enzyme having a stereospecific esterase activity for (S)-N-benzyl-3-acyloxypyrrolidine of the formula (S)-[I]:

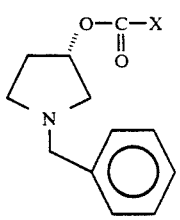
(S)-[I]

wherein X is as defined as above; and (2) separating from the hydrolysate in the foregoing step (1), (R)-N-benzyl-3-hydroxypyrrolidine of the formula (S)-[II] and (R)-N-benzyl-3-acyloxypyrrolidine of the formula (R)-[I]:

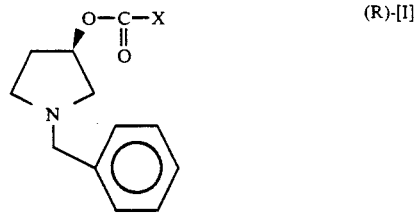
(R)-[I]

wherein X is as defined above.

3. A method according to claim 1, wherein said microorganisms or enzyme with stereo-specific esterase activity are immobilized on a water-insoluble carrier or support.

4. A method according to claim 1, wherein said optically active (R)-N-benzyl-3-hydroxypyrrolidine and said optically active (S)-N-benzyl-3-acyloxypyrrolidine are separated form each other by column chromatography with an inorganic or synthetic adsorbent used as a support.

5. A method according to claim 1, wherein said optically active (S)-N-benzyl-3-acyloxypyrrolidine is separated from said optically active (R)-N-benzyl-3-hydroxypyrrolidine by extraction with a hydrophobic solvent.

6. A method according to claim 2, wherein said microorganisms or enzyme having stereospecific esterase activity are immobilized on water-insoluble carrier or support.

7. A method according to claim 2, wherein said optically active (S)-N-benzyl-3-hydroxypyrrolidine and said optically active (R()-N-benzyl-3-acyloxypyrrolidine are separated from each other by column chromatography with an inorganic or synthetic adsorbent used as a support.

8. A method according to claim 2, wherein said optically active (R)-N-benzyl-3-acyloxypyrrolidine is separated from said optically active (S)-N-benzyl-3-hydroxypyrrolidine by extraction with a hydrophobic solvent.

* * * * *